(12) United States Patent
Bastawade et al.

(10) Patent No.: US 6,448,051 B1
(45) Date of Patent: Sep. 10, 2002

(54) PROCESS FOR THE PREPARATION OF 4(R)-HYDROXY CYCLOPENT-2-EN1(S)-ACETATE

(75) Inventors: Kulbhussan Balwant Bastawade; Digambar Vitthal Gokhale; Ravindranathan Thottapillil; Sandeep Raghunath Ghorpade; Rohini Ramesh Joshi; Uttam Ramrao Kalkote, all of Pune (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 09/747,498

(22) Filed: Mar. 15, 2001

(51) Int. Cl.$^7$ .................................................. C12P 7/62
(52) U.S. Cl. ........................ 435/135; 435/917; 435/942
(58) Field of Search ................................. 435/135, 917, 435/942

(56) References Cited

U.S. PATENT DOCUMENTS 4,008,125 A * 2/1977 Kurozumi et al. .......... 435/135
4,618,690 A * 10/1986 Schneider et al. .......... 556/441

OTHER PUBLICATIONS

Computer Caplus Abstract 1976:541335 Miura et al DE2552871 PUB Nov. 1975.*
ACS Registry RN–60176–77–4 2001.*
Computer BIOTECHDS Abstract 2000–11907 Kalkote et al Tetrahedron Asymmetry (2000) 11, 14 2965–70.*

* cited by examiner

*Primary Examiner*—Herbert J. Lilling
(74) *Attorney, Agent, or Firm*—Ladas & Parry

(57) ABSTRACT

The present invention relates to a process for the preparation of 4-(R)-hydroxycyclopent-2-en-1 (S)-acetate of the formula 2

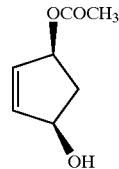

Formual 2 by reacting meso-cyclopent-2-en-1, 4-diacetate of formula 1

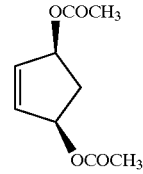

Formula 1 with a whole cell enzyme in a mixture of a buffer and an organic solvent, filtering the reaction mixture to remove the enzyme, extracting the resultant compound with an organic solvent, and removing the solvent to obtain the desired product.

7 Claims, No Drawings

PROCESS FOR THE PREPARATION OF 4(R)-HYDROXY CYCLOPENT-2-EN1(S)-ACETATE

BACKGROUND OF THE INVENTION

1. Field of the invention

The present invention relates to a process for the preparation of 4(R)-hydroxycyclopent-2-en-1(S)-acetate of the formula 2 below.

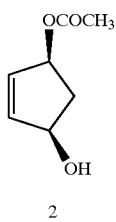

More particularly the present invention relates to a process for the enzymatic preparation of 4-(R)-hydroxycyclopent-2-en-(S)acetate of the formula 2 from meso-cyclopent-2-en-1,4-diacetate of the formula 1 below.

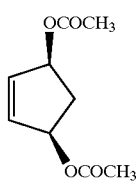

2. Description of Related Art 4-(R)-hydroxycyclopent-2-en-1(S)-acetate is an important intermediate in the synthesis of biologically active cyclopentenoid natural products such as prostaglandins, prostacyclins, thromboxane (Harre, M., Raddatz. P., Walenta, R, Winterfeldt, E. Angew. Chem; 1982, 94, 496).

Other known processes for the preparation of 4-(R)-hydroxycyclopent-2-en-1(S)acetate involves the enantioselective hydrolysis of meso-cyclopent-2-en-1,4-diacetate using Pig Liver Esterase (PLE) (Y. F. Wang, C. S. Chen, G. Girdankas, C. J. Sih; J. Am. Chem. Soc. 1984, 106, 3695), and the trans esterification of cyclopent-2-ene-1,4-diol to 4(R)-hydroxycyclopent-2-en-1(S)-acetate (Johnson, Braun, Organic Synthesis, 1995, 73, 36). The known processes described above use costlier pig liver esterase (PLE).

The main object of the present invention is to provide a new process for the preparation of 4-(R)-hydroxycyclopent-2-en-1(S)-acetate which obviates the drawbacks of the prior known processes by using a more easily available microbial whole cell enzyme.

Another object is to provide a new process for the enantioselective hydrolysis of meso-cyclopent-2-en-1,4-diacetate using micro-organisms as whole cell enzyme from the National Collection of Industrial Micro-organisms (NCIM), NCL Pune.

BRIEF SUMMARY OF THE INVENTION

Accordingly, the present invention provides a process for the preparation of 4-(R)hydroxycyclopent-2-en-1(S)-acetate of the formula 2

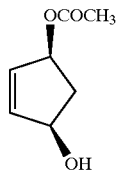

which comprises:

reacting meso-cyclopent-2-en-1,4-diacetate of formula 1

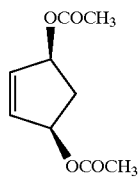

with a whole cell enzyme in a mixture of a buffer and an organic solvent, wherein the buffer to organic solvent ratio being in the range of from 4:1 to 24:1;

stirring the reaction mixture at a temperature ranging between 25–30° C. for a period ranging from 10–16 hrs;

filtering the reaction mixture to remove the enzyme;

extracting the resultant compound with an organic solvent; and removing the solvent to obtain the desired product.

In one embodiment of the invention the buffer used is selected from phosphate buffer and citrate buffer.

In a further embodiment of the invention the concentration of the buffer is in the range of 0.05M–0.1M.

In yet another embodiment of the invention the pH of the buffer is in the range of 6.0–8.0.

In another embodiment of the invention the organic solvent used for the reaction is selected from the group consisting of methanol, ethanol, propanol, butanol, isopropanol, acetone, dimethylsulpoxide (DMSO) and dimethylformamide (DMF).

In another embodiment of the invention the organic solvent used for the extraction of the product is selected from the group consisting of ether, ethyl acetate, chloroform and any mixtures thereof.

In a further embodiment of the invention, the whole cell enzyme used is selected from the group consisting of *Aspergillis oryzae, Aspergillus oryzae, Aspergillus sojae, Aspergillus oryzae, Aspergillus parasiticus, Trichosporon beigelii, Trichosporon beigeii*, Trichosporon sp., Trichosporon sp. and *Trichosporon capitatum*.

In another embodiment of the invention, the chemical yield of 4-(R)hydroxycyclopent-2-en-1(S)-acetate is 83% and its optical purity is 99%.

DETAILED DESCRIPTION OF THE INVENTION 4-(R)-hydroxycyclopent-2-en-1(S)-acetate of the formula 2

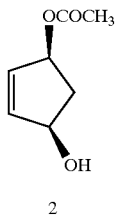

Formula 2 is prepared by reacting meso-cyclopent-2-en-1,4-diacetate of formula 1

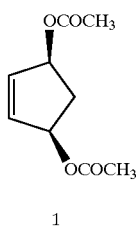

Formula 1 with a whole cell enzyme obtained from NCIM, Pune in a mixture of a buffer and an organic solvent, wherein the buffer to organic solvent ratio being in the range of from 4:1 to 24:1. The reaction mixture is then shrred at a temperature ranging between 25–30° C. for a period ranging from 10–16 hrs, and the reaction mixture is subsequently filtered to remove the enzyme. The resultant compound is then extracted with an organic solvent and the solvent removed.

The buffer used is selected from phosphate buffer and citrate buffer, wherein the concentration of the buffer being in the range of 0.05 M–0.1 M. The pH of the buffer is in the range of 6.0–8.0. Preferably, the pH of the phosphate buffer is in the range of 6.0 to 8.0 and that of the citrate buffer is in the range of 6.0 to 7.5.

The organic solvent used for the reaction is selected from methanol, ethanol, propanol, butanol, isopropanol, acetone, dimethylsulpoxide (DMSO) and dimethylformamide (DMF). The organic solvent used for the extraction of the final product is selected from the group consisting of ether, ethyl acetate, chloroform and mixtures thereof.

The whole cell enzyme used is selected from the group consisting of *Aspergillus oryzae, Aspergillus oryzae, Aspergillus sojae, Aspergillus oryzae, Aspergillus parasiticus, Trichosporon beigelli, Trichosporon beigeii,* Trichosporon sp. and *Trichospoon capitalum.* (NCIM Nos. 634, 637, 639, 929,1212, 3326 (ATCC Patent Deposit Designation PTA-3079), 3404, 3369, 3404 and 3412). This group is available to the public.

The chemical yield of 4-(R)-hydroxycyclopent-2-en-1 (S)-acetate is 83% and its optical purity is 99%.

The merits of the process of the present invention are the use of easily accessible microorganisms from NCIM, Pune and a high optical purity of the product. The cost of whole cell enzyme (micro-organism) compared to PLE is much less.

The process of the present invention is described herein below with references to following examples, which are illustrative only and should not be construed to limit the scope of the present invention in any manner.

EXAMPLE 1

General Procedure for Cell Biomass Preparation (Whole Cell Enzyme):

The inoculum (5–10 ml) was developed by growing the microorganisms in a medium containing malt extract (0.3%), Glucose (1%), Yeast extract (0.3%) and peptone (0.5%) at a pH of 6.8–7.0 for 48 hours with shaking at 150–180 rpm. This inoculum was then transferred to a growth medium containing $K_2H_2PO_4$ (0.2%), Yeast extract (0.1%), Peptone (0.5%), KCl (0.05%), $NaNO_3$ (0.05%), $MgSO_4.7H_2O$ (0.05%), and Olive oil (1.0%) at a pH of 5.5 and incubated at 28–30° C. for 36–48 hours on rotary shakers (180–200 rpm.). The grown cells were then separated by certification and the biomass was used for the reaction.

EXAMPLE 2

General Procedure for Enantioselective Hydrolysis of meso-cyclopent-2-ene-1,4-Diacetate.

0.200 gms (0.001 mole parts) of meso-cyclopent-2-en-1, 4-diacetate (1) was suspended in a phosphate buffer (10 parts) and 100 mg of wet cell mass (micro-organisms, mentioned in Table 1) was added and stirred for 24 hrs. The cell mass was then removed by filtration through celite and the compound was extracted with an ethyl acetate:ether mixture (1:1, 2×20 parts). Upon evaporation of the solvent, hydroxycyclopentene acetate (2) was obtained. The results of the 10 micro-organisms used as enzyme are tabulated in Table 1.

EXAMPLE 3

General Procedure for Enantioselective Hydrolysis of meso-cyclopent-2-ene-1,4-Diacetate.

0.200 gms (0.001 mole parts) of meso-cyclopent-2-en-1, 4-diacetate (1) was suspended in a mixture of phosphate buffer (9 parts) and organic solvent (1 part as mentioned in table 2). 100 mg of wet cell mass (NCIM 3326) (ATTC Patent Deposit Designation PTA-3079) was added and stirred for 24 hrs at an ambient temperature. The cell mass was then removed by filtration through celite and the compound was extracted with an ethyl acetate:ether mixture (1:1,2×20 parts). Upon evaporation of the solvent, hydroxy cyclopentene acetate (2) was obtained. The results are tabulated in Table 2.

EXAMPLE 4

General Procedure for Enantioselective Hydrolysis of meso-cyclopent-2-en-1,4-Diacetate using enzyme (NCIM 3326).

0.200 gms (0.001 parts) of meso-cyclopent-2-en-1,4-diacetate (1) was suspended in a mixture of phosphate buffer and ethanol as mentioned in Table 3 (10 parts) and 100 mg of wet cell mass (NCIM 3326) (ATTC Patent Deposit Designation PTA-3079) was added and stirred for 24 hrs. The cell mass was removed by filtration through celite and the compound was extracted with an ethyl acetate:ether mixture (1:1, 2×20 parts). Upon evaporation of the solvent, hydroxycyclopentene acetate (2) was obtained. The results of different proportion of ethanol are tabulated in Table 3.

EXAMPLE 5

General Procedure for Enantioselective Hydrolysis of meso-cyclopent-2-en-1,4-Diacetate Using Different Enzyme in Buffer:Ethanol(9:1 ratio)

0.200 gms (0.001 parts) of meso-cyclopent-2-en-1,4-diacetate (1) was suspended in a mixture of phosphate buffer and ethanol (10 parts). 100 mg of wet cell mass as mentioned in table 4 was added and stirred for 24 hrs. The cell mass was removed by filtration through celite and the compound was extracted with and ethyl acetate:ether mixture (1:1, 2×20 parts). Upon evaporation of the solvent, hydroxycyclopentene acetate (2) was obtained. The results of different micobial whole cell enzymes in buffer: ethanol (9:1) are tabulated in Table 4.

EXAMPLE 6

General Procedure for Enantioselective Hydrolysis of meso-cyclopent-2-en-1,4-diacetate Using Enzyme NCIM 3326, 3404.

5.0 parts (0.027 mole parts) meso-cyclopent-2-en-1,4-diacetate (1) was suspended in a mixture of 400 parts phosphate buffer and 100 parts ethyl alcohol in a 1 liter pH stat fermenter equipped with a auto burette containing 1N KOH and a stirrer. Cell-mass (wet weight=5 parts) was added to the fermenter and the reaction mixture was stirred at room temperature (30±1° C.). The pH of the reaction was maintained at 7 by the continuous addition of 1N KOH for 10 hrs. After completion of the reaction, the reaction mixture was centrifuged to remove the cell mass and the superenent liquid was extracted with a ether-ethyl acetate solvent (1:1; 3×100 parts). Upon evaporation of solvent under a reduced pressure, the crystalline product 4(R)-hydroxycyclopent-2-en-1(S)-acetate-(2, 3.12 parts, 81.3%) was obtained. Crystallization with ether:Pet ether yielded a product having 99% optical purity.

a: 1(0.050 g, 0.27 mmol) was reacted with wet cell cultures in a 0.1 M phosphate bufer (5 ml)for 18 hr at 30° C. on an orbital shaker. b: rotations were measured in chloroform using 1% concentration. $[\alpha]_D$ of 2=−69.3 (c 1, chloroform).
*(ATTC Patent Deposit Designation PTA-3079)

TABLE 1

Results of preliminary screening[a]

| No. | Culture Name | NCIM No. | Chemical Yield of 2% | $[\alpha]_D$[b] | Optical purity % of 2 |
|---|---|---|---|---|---|
| 1. | Trichosporon beigelii | 3326* | 88 | −20.2 | 29.1 |
| 2. | Trichosporon sp. | 3369 | 75 | −5.8 | 8.4 |
| 3. | Trichosporon sp. | 3382 | 78 | −5.5 | 7.9 |
| 4. | Trichosporon beigeii | 3404 | 76 | −15.6 | 22.5 |
| 5. | Trichosporon captatum | 3412 | 78 | −16.4 | 23.7 |
| 6. | Aspergillus oryzae | 634 | 85 | +37.8 | 54.6 |
| 7. | Aspergillus oryzae | 637 | 81 | +50.2 | 72.4 |
| 8. | Aspergillus sojae | 643 | 86 | +33.7 | 48.7 |
| 9. | Aspergillus oryzae | 929 | 85 | +36.5 | 52.6 |
| 10. | Aspergillus parasiticus | 1212 | 79 | +36.6 | 52.8 |

[a]1 (0.050 g, 0.27 mmol) was reacted with wet cell cultures in a 0.1 M phosphate buffer (5 ml) for 18 hr at 30° C. on an orbital shaker.
[b]rotations were measured in chloroform using 1% concentration. $[\alpha]_D$ of 2 = 69.3 (c 1, chloroform).
*(ATTC Patent Deposit Designation PTA-3079)

TABLE 2

Hydrolysis of 1 catalyzed by NCIM 3326[a]

| No. | Co-solvent | Yield of 2% | $[\alpha]_D$) of 2 | Optical purity of 2% |
|---|---|---|---|---|
| 1. | Methanol | 76 | −39.5 | 57.0 |
| 2. | Ethanol | 83 | −57.2 | 82.6 |
| 3. | 2-Propanol | 79 | −42.9 | 61.9 |

TABLE 2-continued

Hydrolysis of 1 catalyzed by NCIM 3326[a]

| No. | Co-solvent | Yield of 2% | $[\alpha]_D$) of 2 | Optical purity of 2% |
|---|---|---|---|---|
| 4. | 1-Butanol | 81 | −14.4 | 20.8 |
| 5. | Acetone | 84 | −45.3 | 65.4 |
| 6. | Dimethylsulphoxide | 77 | −21.4 | 30.9 |
| 7. | Dimethylformamide | 75 | 34.9 | 50.4 |

[a]All the reactions were carried out at 30° C. on orbital shaker for 18 hr using 1% concentration of substrate 1 in 0.1 M phosphate buffer (pH 7) containing 10% v/v of cosolvent.

TABLE 3

Effect of variation of ethanol concentration on the hydrolysis of 1 catalyzed by NCIM 3326.

| No. | Ethanol concentration % | Yield of 2% | $[\alpha]_D$) of 2 | Optical purity of 2% |
|---|---|---|---|---|
| 1. | 4 | 81 | −48.6 | 70.1 |
| 2. | 10 | 83 | −57.2 | 82.6 |
| 3. | 20 | 79 | −54.5 | 78.6 |
| 4. | 50 | No reaction | — | — |
| 5. | 80 | No reaction | — | — |

TABLE 4

Effect of 10% v/v ethanol in buffer media on the hydrolysis of 1 catalyzed by cultures from Trichosporon species.

| No. | Culture (NCIM No.) | Yield of 2% | $[\alpha]_D$) of 2 | Optical purity of 2% |
|---|---|---|---|---|
| 1. | 3326* | 83 | −57.2 | 82.6 |
| 2. | 3369 | 78 | −54.4 | 78.6 |
| 3. | 3382 | 75 | −45.3 | 65.4 |
| 4. | 3404 | 74 | −59.5 | 85.9 |
| 5. | 3412 | 79 | −53.5 | 77.3 |

*(ATTC Patent Deposit Designation PTA-3079)

The ratio of phosphate buffer (0.05M, pH 7) to ethanol is 9:1

1. Our process gives a product ie 4(R)-hydroxy-cyclopent-2-en-1(S)-acet-ate (2) of high optical purity than reported with pig liver esterase,which is an important key intermediate of Corey lactone, Noyori lactone and prostaglandins 2. Our process involves the use of crude enzyme, which is very cheap and easily available.

I claim:
1. Process for the preparation of 4-(R)-hydroxycyclopent-2-en-1(S)-acetate of the formula 2

Formula 2

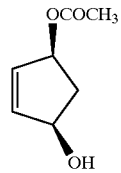

which comprises reacting meso-cyclopent-2-en-1,4-diacetate of formula 1

Formula 1

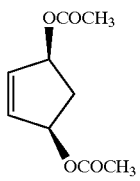

with a whole cell enzyme selected from the group consisting of *Trichosporon beigelii, Trichosporon beigeii*, Trichosporon sp., Trichosporon sp. and *Trichosporon capitatum* in a mixture of a buffer and an organic solvent, the buffer to organic solvent ratio being in the range of from 4:1 to 24:1, stirring the reaction mixture at a temperature ranging between 25–30° C. for a period ranging from 10–16 hrs, filtering the reaction mixture to remove the enzyme and extracting the resultant compound with all organic solvent, removing the solvent to obtain the desired product.

2. A process as claimed in claim wherein the buffer used is selected from phosphare buffer and cirrate.

3. A process as claimed in claim 2 wherein the concentration of the buffer is the range of 0.05M–0.1M.

4. A process as claimed in claim 2 wherein the pH of the buffer is in the range of 6.0–8.0.

5. A process as claimed in claim 1 wherein the organic solvent used for the reaction is selected from the group consisting of methanol, ethanol, propanol, butanol, isopropanol, acetone, dimethylsulpoxide (DMSO) and dimethylformamide (DMF).

6. A process as claimed in claim 1, wherein the organic solvent used for the extraction of the product is selected from the group consisting of ether, ethyl acetate, chloroform and mixtures thereof.

7. A process as claimed in claim 1 wherein the chemical yield of 1-(R) hydroxycyclopent-2-en-1(S)-acetate is 83% and its optical purity is 99%.

* * * * *